United States Patent
Leung et al.

(10) Patent No.: US 9,840,526 B1
(45) Date of Patent: Dec. 12, 2017

(54) IRIDIUM(III)-BASED IRREVERSIBLE PROTEIN-PROTEIN INTERACTION INHIBITOR OF BRD4 AS A POTENT ANTICANCER AGENT

(71) Applicants: University of Macau, Taipa, Macau (CN); Hong Kong Baptist University, Kowloon (HK); Kaohsiung Medical University, Kaohsiung (TW)

(72) Inventors: Chung-Hang Leung, Macau (CN); Hai-Jing Zhong, Macau (CN); Dik-Lung Ma, Kowloon (HK); Hui-Min Wang, Kaohsiung (TW)

(73) Assignees: University of Macau (MO); Hong Kong Baptist University, Kowloon (HK); Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 15/661,288

(22) Filed: Jul. 27, 2017

Related U.S. Application Data

(60) Provisional application No. 62/368,194, filed on Jul. 29, 2016.

(51) Int. Cl.
  *C07F 15/00* (2006.01)
  *A61K 31/555* (2006.01)
(52) U.S. Cl.
  CPC .................. *C07F 15/0033* (2013.01)
(58) Field of Classification Search
  CPC .............................. C07F 15/00; A61K 31/555
  USPC ............................................... 546/2; 514/188
  See application file for complete search history.

(56) References Cited

U.S. PATENT DOCUMENTS 7,005,522 B2 * 2/2006 Deaton ............... C07F 15/0033
                                                        428/690

OTHER PUBLICATIONS

Zhong, H-J. et al.: A rhodium(III) complex as an inhibitor of neural precursor cell expressed, developmentally down-regulated 8-activating enzyme with in vivo activity against inflammatory bowel disease, J. med. Chem., vol. 60, pp. 497-503, 2017.*

* cited by examiner

*Primary Examiner* — Charanjit Aulakh
(74) *Attorney, Agent, or Firm* — Ladas & Parry LLP

(57) ABSTRACT

Bromodomain-containing protein 4 (BRI)) has recently emerged as an attractive epigenetic target for anticancer therapy. Iridium(III) complexes are useful as irreversible inhibitor of BRD4. Complex 1a of the formula:

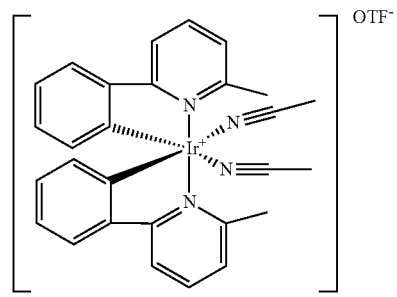

is particularly useful.

14 Claims, 6 Drawing Sheets

IRIDIUM(III)-BASED IRREVERSIBLE PROTEIN-PROTEIN INTERACTION INHIBITOR OF BRD4 AS A POTENT ANTICANCER AGENT

CROSS REFERENCE APPLICATION

The present application claims priority from provisional application 62/368,194 filed on Jul. 29, 2016, the entire contents of which are incorporated herein by reference.

FIELD OF THE INVENTION

The present invention relates to iridium (III) complexes having protein-protein interaction inhibition properties useful in treating cancer.

BACKGROUND

Gene transcription is a dynamic process tightly regulated by chromatin, which is a complex structure comprised of DNA and histone proteins.[1] The function of gene regulation is controlled by post-translational modification states of DNA-packing histones in the chromatin complex.[2] For example, the N-terminal lysine residues of histone proteins can be acetylated and deacetylated to control gene expression via the interplay of a range of enzymes such as histone acetyltransferase (HAT), histone deacetylase (HDAC) and methyltransferase (MT).[1] Hence, these enzymes have become the targets of drug discovery efforts.[3,4] However, the reader domains that interrogate post-translational modification states have been less intensively pursued as epigenetic targets.[5,6]

Acetylated histones are recognized by small protein pockets called bromodomains.[7] The bromodomain and extraterminal domain (BET) family of bromodomain-containing proteins (BRD2, BRD3, BRD4 and BRDT) are a class of transcriptional regulators containing tandem bromodomains and a carboxyl-terminal recruitment domain.[8,9] In particular, BRD4 plays a significant role in cell cycle progression and viability via its effects on growth-related genes at the M/G1 boundary.[10,11] Recently, BRD4 has been shown to play an important role in sustaining the proliferation of metastatic melanoma, a mostly incurable disease, thus rendering it as a possible target for epigenetic therapy.[12]

The selective inhibition of the bromodomain 4 (BRD4)/histone interaction has been demonstrated by several small molecule inhibitors such as (+)-JQ1, which is capable of occupying the ε-N-acetylated lysine residue (Kac) binding site of BRD4 and act as a Kac-competitive inhibitor.[13] Subsequent reports have shown that (+)-JQ1 can directly regulate transcription mediated by the c-myc gene and reduce the expression of oncogenic c-myc protein.[14,15]

The success of the anti-cancer compound cisplatin and its analogues has inspired the investigation of metal-based compounds as therapeutic agents over the past few decades.[16-24] While classical metal-based chemotherapeutic agents typically target double-helical DNA, increasing knowledge in molecular biology has uncovered the possibility of specifically targeting therapeutically relevant proteins or enzymes using transition metal complexes.[25-29] Metal-based compounds can offer distinct opportunities in targeting proteins or enzymes compared to organic small molecules due to their interesting structural diversity and electronic properties. Moreover, metal complexes can undergo ligand exchange reactions with biomolecules, and such irreversible inhibitors may show enhanced potency and potentially allow for less frequent and lower dosages in vivo.[30] Examples of approved drugs that act via a covalent mechanism include EGFR inhibitors neratinib (Pfizer), afatinib/BIBW-2992 (Boehringer Ingelheim) and PF-00299804 (Pfizer), and anti-HCV agents telaprevir (Vertex Pharmaceuticals and Johnson & Johnson) and boceprevir/Victrelis (Merck) (FIG. S1).[30] Neratinib, Afatinib/BIBW-2992 and PF-00299804 target cysteine in EGFR and carfilzomib/Kyprolis, a selective proteasome inhibitor, targets threonine, while Telaprevir, used for the treatment of HCV, targets serine. Boceprevir/Victrelis also targets serine of HCV protease, and is used for the treatment of hepatitis caused by HCV, Metal complexes can adopt a wide range of geometrical shapes defined by the oxidation state of the metal center and the nature of the co-ligands, while organic compounds are mainly restricted to linear, trigonal planar and tetrahedral geometries, Therefore, metal complexes may be able to sample additional chemical space within the active site of enzymes or proteins, In addition, the steric and electronic properties of metal complexes can be easily tuned without lengthy synthetic protocols due to the modular nature of inorganic synthesis, We and others have previously demonstrated that certain Ir(III),[31-33] Rh(III)[34,35] and Ru(II)[36-39] complexes can be developed as inhibitors of enzymes or protein-protein interactions (PPI). In particular, Ma et al Angew. Chem. Int. Ed. Engl, 47, pages 3735-3739 (2008) reported that binds covalently to histidine and generates a luminescence signal.

SUMMARY OF THE INVENTION

Form a first aspect, the present invention provides compounds of the formula:

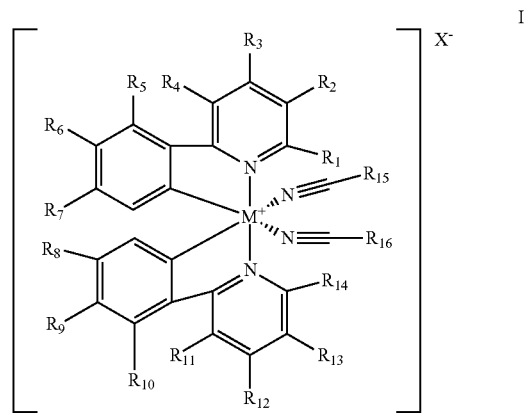

wherein $X^-$ is an anion selected from trifluoromethanesulfonate, hexafluorophosphate, chloride, perchlorate, tetrafluoroborate tetraphenyl borate, or substituted tetraphenyl borate such as tetra[3,5-bis(trifluoromethyl)phenyl] borate M is iridium;

$R_1$ and $R_{14}$ are each individually selected from the group consisting of methyl and ethyl;

$R_2$, $R_3$ $R_6$, $R_{12}$ and $R_{13}$ are each individually selected from the group consisting of hydrogen, alkyl and alkoxy groups containing from 1-6 carbon atoms wherein the alkyl group is linear or branched;

$R_7$ and $R_8$ are each individually selected from the group consisting of hydrogen, CHO, alkyl of from 2-6 carbon atoms and alkoxy groups containing from 1-6 carbon atoms wherein the alkyl group is linear or branched $R_4$ and $R_5$ are each individually selected from the group consisting of hydrogen, alkyl and alkoxy groups containing from 1-6 carbon atoms wherein the alkyl group is linear or branched or R4 and R5 can jointly form a CH=CH or $CH_2$—$CH_2$ group; and $R_{10}$ and $R_{11}$ are each individually selected from the group consisting of hydrogen, alkyl and alkoxy groups containing from 1-6 carbon atoms wherein the alkyl group is linear or branched or $R_{10}$ and $R_{11}$ can jointly form a CH=CH or $CH_2$—$CH_2$ group;

$R_{15}$ and $R_{16}$ are each individually selected from alkyl groups of from 1-4 carbon atoms or aryl groups of 6-10 carbon atoms, provided that at least one of $R_1$-$R_{14}$ is not hydrogen.

From a second aspect, the invention provides a method for inhibiting protein-protein interaction in a patient in need thereof which comprises administering to a patient in need thereof a therapeutic dose of such a compound of the formula:

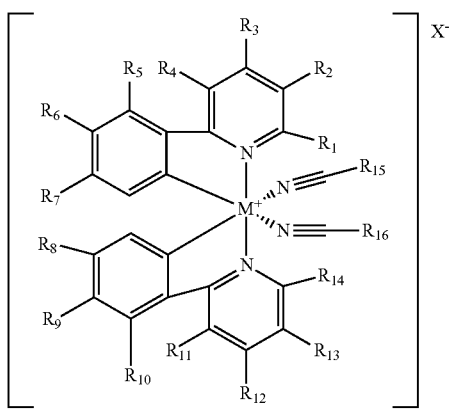

wherein $X^-$ is an anion selected from trifluoromethanesulfonate, hexafluorophosphate, chloride, perchlorate, tetrafluorohorate tetraphenyl borate, or substituted tetraphenyl borate such as tetra[3,5-biqtrifluoromethyl)phenyl] borate M is iridium or rhodium;

$R_1$ and $R_{14}$ are each individually selected from the group consisting of methyl and ethyl;

$R_2$, $R_3$ $R_6$, $R_9$, $R_{12}$ and $R_{13}$ are each individually selected from the group consisting of hydrogen, alkyl and alkoxy groups containing from 1-6 carbon atoms wherein the alkyl group is linear or branched;

$R_7$ and $R_8$ are each individually selected from the group consisting of hydrogen, CHO, alkyl of from 1-6 carbon atoms and alkoxy groups containing from 1-6 carbon atoms wherein the alkyl group is linear or branched $R_4$ and $R_5$ are each individually selected from the group consisting of hydrogen, alkyl and alkoxy groups containing from 1-6 carbon atoms wherein the alkyl group is linear or branched or R4 and R5 can jointly form a CH=CH or $CH_2$—$CH_2$ group; and $R_{10}$ and $R_{11}$ are each individually selected from the group consisting of hydrogen, alkyl and alkoxy groups containing from 1-6 carbon atoms wherein the alkyl group is linear or branched or $R_{10}$ and $R_{11}$ can jointly form a CH=CH or $CH_2$—$CH_2$ group; and $R_{15}$ and $R_{16}$ are each individually selected from alkyl groups of from 1-4 carbon atoms or aryl groups of 6-10 carbon atoms

DETAILED DESCRIPTION OF THE INVENTION

Preferably for both aspects of the invention, the compound has the following stereochemistry:

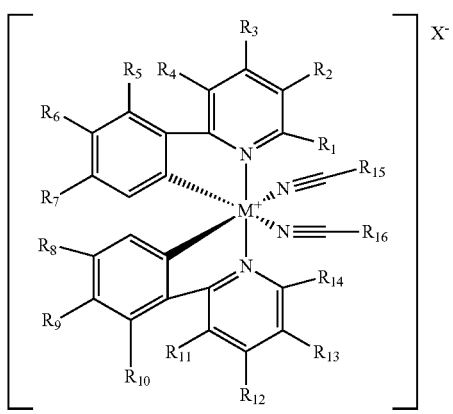

In both aspects of the invention, it is preferred that M is iridium.

Preferred compounds include those wherein:

$R_{15}$ and $R_{16}$ are both lower alkyl, of 1-3 carbon atoms, such as methyl;

$R_1$ and $R_{14}$ are both lower alkyl of 1-3 carbon atoms such as methyl and $R_2$-$R_{13}$ are all hydrogen;

$R_7$ and $R_8$ are both lower alkyl of 1-3 carbon atoms such as methyl or are CHO and $R_2$-$R_6$ and $R_8$-$R_{13}$ are all hydrogen.

A particularly preferred compound for both aspects of the invention is of the formula:

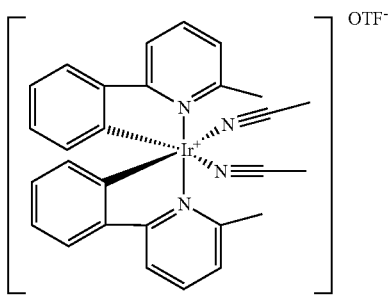

wherein OTF indicates that the compound is a trifluoromethanesulfonate salt.

This compound is hereinafter referred to as Compound 1(a).

Figure 1:
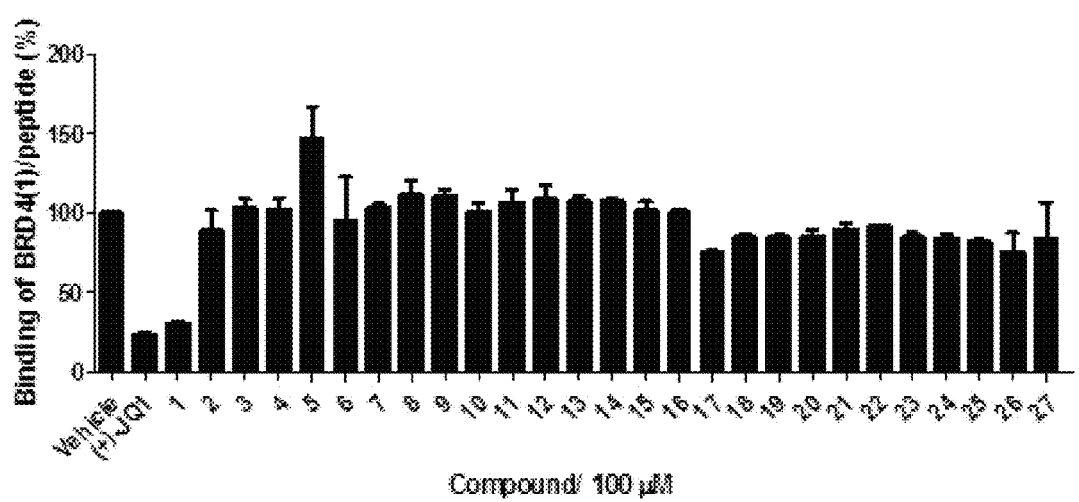
FIG. 1 shows displacement of a tetra-acetylated H4 peptide from BRD4 by a selection of Ir(III)/Rh(III) complexes at 100 μM in a TR-FRET assay. Error bars represent the standard deviations of the results from three independent experiments.
Figure 2:
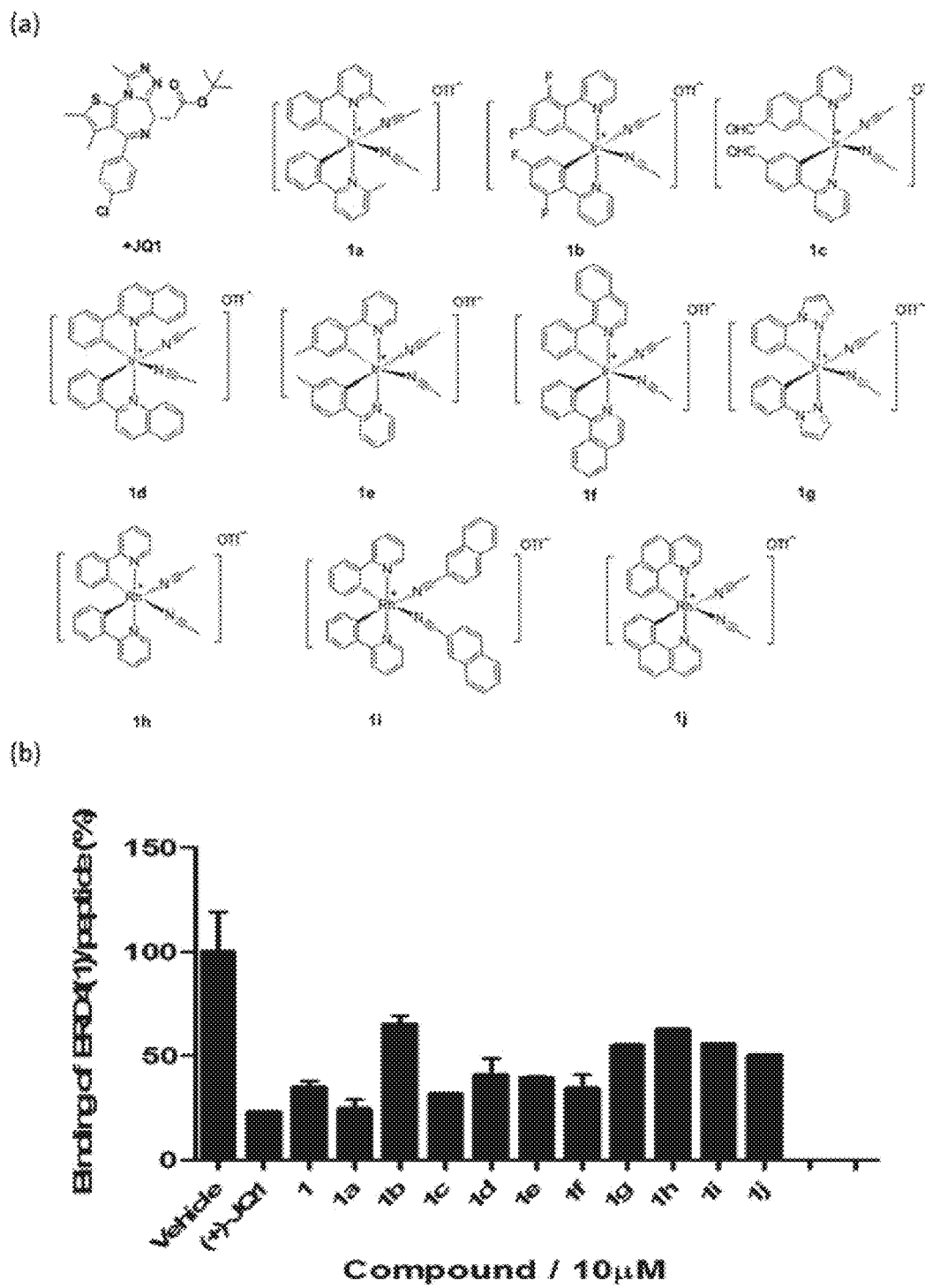
FIG. 2 shows (a) Chemical structures of the cyclometallated Ir(III) and Rh(III) complexes (racemates) used for structure-activity analysis (SAR). (b) Displacement of a tetra-acetylated H4 peptide from BRD4 by complex 1 and analogues 1a-1j at 10 μM in a TR-FRET assay. Error bars represent the standard deviations of the results from three independent experiments.

Notably, complex 1a, as noted above and shown in FIG. 2, which contains two 2-phenyl-6-methylpyridine C^N ligands and two acetonitrile ligands, was more potent than the parent complex (Compound 1) wherein the C^N ligand was 2-phenyl-pyridine. Based on these results, preliminary structure-activity relationships (SAR) could be deduced. Varying the N-donor ligands from acetonitrile to other nitrile-based ligands (such as in 1i) did not result in improved activity against BRD4, as complex 1i was one of the least active compounds in the TR-FRET assay. Additionally, substituting the 2-phenyl-6-methylpyridine (as in 1a) or 2-phenylpyridine (as in 1) C^N co-ligands with more extended aromatic systems such as 2-phenylquinoline (as in 1d) or 1-phenylisoquinoline (as in 1f) also decreased the potency of the complex. Moreover, the presence of fluorine substituents on the C^N ligands appeared to be highly detrimental for activity, as complex 1b showed the weakest activity out of this series. Finally, replacing the iridium(III) center of complex 1 with rhodium(III) (as in congener 1h) resulted in greatly decreased activity against BRD4. Taken together, these results suggest that the binding between 1a and BRD4 is highly sensitive to the steric and/or electronic properties of the metal complexes.

Methods of the present invention provide BRD4 inhibition which we hypothesize derives from cleavage of the $NCR_{15}$ and $NCR_{16}$ groups from the active compounds leading to covalent bonding with the protein target. In this way, the compounds inhibit protein-protein interaction between BRD4 and acetylated histone peptides, which is of particular importance in combatting cancers such as melanoma.

The iridium(III) complex 1a was found to be a potential modulator of the epigenetic reader protein BRD4. Complex 1a inhibited the PPI between BRD4 and an acetylated histone peptide as revealed by multiple biochemical assays, including FRET, AlphaScreen and FP assays. Although mass spectrometry data suggested that 1a binds to histidine residues with the loss of ACN ligands, 1a was found not to significantly interact with other histidine-containing proteins such as caspase-6 and STAT3. Additionally, complex 1a displaced BRD4 from chromatin and hence inhibited c-myc expression in melanoma cells through blocking the binding of BRD4 to the c-myc promoter. Cytotoxicity and colony formation experiments suggested 1a is capable of antiproliferative activity in melanoma cells, possibly through down-regulation of c-myc protein expression. Finally, complex 1a significantly repressed A375 melanoma xenograft growth in an in vivo mouse model without causing visible toxicity to the mice. Preliminary structure-activity analysis indicated that the nature of the metal ion and the C^N and N^N T co-ligands were important for the biological activity of 1a. To our knowledge, complex 1a represents the first metal-based inhibitor of BRD4 and of any BET bromodomain-containing protein in general.

In the methods of the present invention, the active compounds are administered by intraperitoneal, intravenous injection or by oral means.

Suitable dosage rates will depend on the individual being treated but are typically in the range 25-200 mg/kg of body weight of the patient, for example 120-189 mg/kg, such as 150 mg/kg. If necessary, a treatment may be repeated.

Suitable compositions for intravenous administration include solutions in aqueous alcohol or dimethyl sulfoxide, one or more additional components such as pharmaceutically acceptable diluents, adjuvants, carriers, preservatives, favouring's, or other convention additives described herein and/or known in the field.

Compounds of the present invention or of use therein may be prepared by a two-step procedure in which the trichloride of the metal is heated. For example to a temperature of at least 100° C., for example 150° C. in an aqueous water miscible organic solvent such as a glycol ether, for example methoxymethanol under an inert atmosphere with at least a two molar excess of a cyclometallated ligand-fanning compound containing the

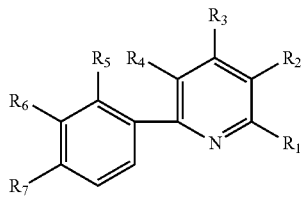

ligand (hereinafter referred to as a C^N ligand) and the product thereof is reacted under an inert atmosphere with a salt (such as a silver salt) of the desired anion and a nitrile of the formula $R_{15}CN$. This reaction may be effected at ambient temperature.

The Invention is Illustrated by the Following Examples

General Synthesis of $[M_2(C^\wedge N)_4Cl_2]$ Complexes where M is Ir(III) or Rh(III)

Cyclometalated dichloro-bridged dimers of the general formula $[M_2(C^\wedge N)_4Cl_2]$, where M=Ir(III)/Rh(III), were synthesized according to a method described by Lowry et al *J. Am. Chem. Soc.*, 2004, 126, 14129-14135. In brief, $MCl_3 \cdot H_2O$ was heated to 150° C. with 2.2 equivalents of cyclometallated C^N ligands in 3:1 methoxymethanol and deionized water under a nitrogen atmosphere for 12 h. The reaction was cooled to room temperature, and the product was filtered and washed with three portions of &ionized water and then three portions of ether (3×50 mL) to yield the corresponding dimer, General synthesis of $[M(C^\wedge N)_2(ACN)_2]OTf$ complexes. These complexes were synthesized according to a method described by Schmid et al, *Inorg. Chem.*, 1994, 33, 9-14 and King et al, *J. Am. Chem. Soc.*, 1985, 107, 1431-1432.2, In brief, $[M_2(C^\wedge N)_4Cl_2]$ was mixed with 2.0 equivalents of silver triflate in 25 mL acetonitrile and stirred at room temperature under a nitrogen atmosphere for 15 h. The mixture was filtered and washed with two portions of ether (2×30 mL) to yield titled product.

The synthesis of $[Rh(ppy)_2(N{\equiv}C{-}R)_2]OTf$ complex. The complex was synthesized according to a literature method.13 In brief, the solution of $[Rh(ppy)_2(ACN)_2]OTf$ (0.08 mmol) and naphthylisocyanide (0.18 mmol) was stirred in acetonitrile (6 mL) overnight under a nitrogen atmosphere. The solvent was removed in vacuo and the residues were washed with diethyl ether (2×50 mL) to yield the titled compound.

General synthesis of $[M(C^\wedge N)_2(N^\wedge N)]PF_6$ complexes. These complexes were synthesized using a modified literature method.1 Briefly, a suspension of $[M_2C^\wedge N)_4Cl_2]$ (0.2 mmol) and corresponding N^N (0.44 mmol) ligands in a mixture of dichloromethane:methanol (1:1, 20 mL) was refluxed overnight under a nitrogen atmosphere. The resulting solution was allowed to cool to room temperature, and was filtered to remove unreacted cyclometallated dimer. To the filtrate, an aqueous solution of ammonium hexafluorophosph.ate (excess) was added and the filtrate was reduced in volume by rotary evaporation until precipitation of the crude product occurred. The precipitate was then filtered and washed with several portions of water (2×50 mL) followed by diethyl ether (2×50 mL). The product was recrystallized by acetonitrile:diethyl ether vapor diffusion to yield the titled compound.

Complex 1a, Yield: 57%. $^1$H NMR (400 MHz, Acetonitrile-$d_3$) δ 7.94-7.92 (m, 4H), 7.62 (d, J=8.0 Hz, 2H), 7.47 (t, J=4.0 Hz, 2H), 6.92 (t, J=4.0 Hz, 2H), 6.76 (t, J=4.0 Hz, 2H), 6.12 (d, J=4.0 Hz, 2H), 2.96 (s, 6H), 2.00 (s, 6H); $^{13}$C NMR (100 MHz, Acetonitrile) δ 167.7, 162.0, 152.4, 145.6, 141.1, 139.0, 131.2, 129,0, 124.0, 123.8, 122.4, 116.6, 27.6; MALDI-TOF-HRMS: Calcd. for C28H26IrN4[M-2ACN-CF3 SO3]+: 529.1256 Found: 529.0762.

Complex 1b. Yield: 59%. $^1$H NMR (400 MHz, Acetonitrile-$d_3$) δ 9.12 (d, J=8.0 Hz, 2H), 8.38 (d, J=8.0 Hz, 2H), 8.16 (t, J=8.0 Hz, 2H), 7.54 (t, J=8.0 Hz, 2H), 6.62 (t, J=8.0 Hz, 2H), 5.56 (t, J=8.0 Hz, 2H), 2.00 (s, 6H); $^{13}$C NMR (100 MHz, Acetonitrile) δ 151.3, 147.5, 139.9, 128.5, 123.9, 123.6, 122.7, 120.2, 119.6, 113.6, 99.1, 98.8, 98.6. MALDI-TOF-HRMS: Calcd. for $C_{26}H_{18}IrN_4[M-2ACN-CF_3SO_3]^+$: 573.0566 Found: 573.0403.

Complex 1c. Yield: 67%. $^1$H NMR (400 MHz, Acetonitrile-$d_3$) δ 9.63 (s, 2H), 9.18 (d, J=8.0 Hz, 2H), 8.25 (d, J=8.0 Hz, 2H), 8.19 (t, J=8.0 Hz, 2H), 7.88 (d, J=8.0 Hz, 2H), 7.62 (t, J=8.0 Hz, 2H), 7.42 (d, J=8.0 Hz, 2H), 6.43 (s, 2H), 2.07 (s, 6H); $^{13}$C NMR (100 MHz, Acetonitrile) δ 164.9, 151.2, 150.3, 142.9, 139.2, 135.9, 130.5, 124.9, 124.8, 124.3, 121.0; MALDI-TOF-HRMS: Calcd. for $C_{28}H_{22}IrN_4$ [M-2ACN-CF$_3$SO$_3$]$^+$: 557.0841 Found: 557.0948.

Complex 1d. Yield: 61%. $^1$H NMR (400 MHz, Acetonitrile-$d_3$) δ 8.81 (d, J=8.0 Hz, 2H), 8.57 (d, J=8.0 Hz, 2H), 8.25 (d, J=8.0 Hz, 2H), 8.10 (d, J=8.0 Hz, 2H), 7.91-7.83 (m, 4H), 7.75 (t, J=8.0 Hz, 2H), 6.97 (t, J=4.0 Hz, 2H), 6.75 (t, J=4.0 Hz, 2H), 6.11 (d, J=4.0 Hz, 2H), 1,97 (s, 6H); $^{13}$C NMR (100 MHz, Acetonitrile) δ 169.9, 147.5, 146.3, 144.0, 140.2, 132.3, 131.4, 129.7, 128.8, 128.0, 126.8, 126.7, 126.0, 122.6, 117.3. MALDI-TOF-HRMS: Calcd. for $C_{34}H_{26}IrN_4[M-2ACN-CF_3SO_3]^+$: 601.1256 Found: 601.4527.

Complex 1f. Yield: 58%. $^1$H NMR (400 MHz, Acetonitrile-$d_3$) δ 9.06-9.03 (m, 4H), 8.29 (d, J=7.6 Hz, 2H), 8.23 (d, J=7.6 Hz, 2H), 7.98-7.88 (m, 6H), 7.02 (t, J=7.6 Hz, 2H), 6,74 (t, J=7.2 Hz, 2H), 6.14 (d, J=8.0 Hz, 2H), 2.07 (s, 6H); $^{13}$C NMR (100 MHz, Acetonitrile) δ 167.5, 146.7, 145.6, 142.4, 137.1, 131.6, 131.2, 129.7, 129.2, 128.5. 127.3, 126,3, 125.8, 121.9, 121.4, 119.2.MALDI-TOF-HRMS: Calcd. for $C_{34}H_{26}IrN_4[M-2ACN-CF_3SO_3]^+$: 601.1256 Found: 601.2065.

Complex 1g. Yield: 67%. $^1$H NMR (400 MHz, Acetonitrile-$d_3$) δ 8.45 (s, 2H), 8.17 (s, 2H), 7.39 (d, J=8.0 Hz, 2H), 6.97 (t, J=8.0 Hz, 2H), 6.90 (d, J=8.0 Hz, 2H), 6.73 (t, J=8.0 Hz, 2H), 6.05 (d, J=8.0 Hz, 2H), 2.00 (s, 6H); $^{13}$C NMR (100 MHz, Acetonittile) δ 142.9, 139.5, 132.5, 127.6, 125.3, 123.0, 111.2, 108.0; MALDI-TOF-HRMS: Calcd. for $C_{22}H_{20}IrN^4[M-2ACN-CF_3SO_3]^-$: 479.0848 Found: 479.0417.

Stability analysis of complexes. Complex 1a was dissolved in DMSO(10 μM) at 298K for 24 h, and was monitored by UV/vis absorbance at 298K for 24 h. Absorption spectra were recorded on a UV-Visible Spectrophotometer (Cary UV-100). For the stability of complex 1a in plasma 20 μM of complex 1a was incubated in 2% (v/v) plasma aqueous solution then monitored by UV-Visible Spectrophotometer.

Competition experiments were carried out by incubating 1a with histidine and 10 equivalents of another natural amino acid. No significant difference was observed between the luminescence intensity detected in the competition experiments compared to that in the presence of histidine alone (data not shown). We further analyzed the binding of 1a to histidine by electrospray ionization mass spectrometry. After incubation of 1a (m/z 529.1) with histidine for 30 min at 20° C., a new peak at m/z 684.2 was observed (FIG. S3b). This peak corresponds to the covalent attachment of one histidine molecule (m/z 155) to 1a. No mass change was recorded for 1a upon incubation with other natural amino acids under same reaction conditions. This data demonstrates that 1a selectively and covalently binds to histidine, leading to a luminescence response.

To assess the selectivity of complex 1a, we tested its activity against two unrelated proteins, caspase-6 and STAT3, which contain 12 and 13 histidine residues, respectively. The results showed that 1a exhibited no significant effect on caspase-6 activity, and only slightly inhibited. STAT3 DNA-binding activity in vitro). This data therefore demonstrates that 1a does not bind equally well to all histidine-containing proteins, and suggests that there exists further criteria that determine the activity of 1a against BRD4.

Figure 4:
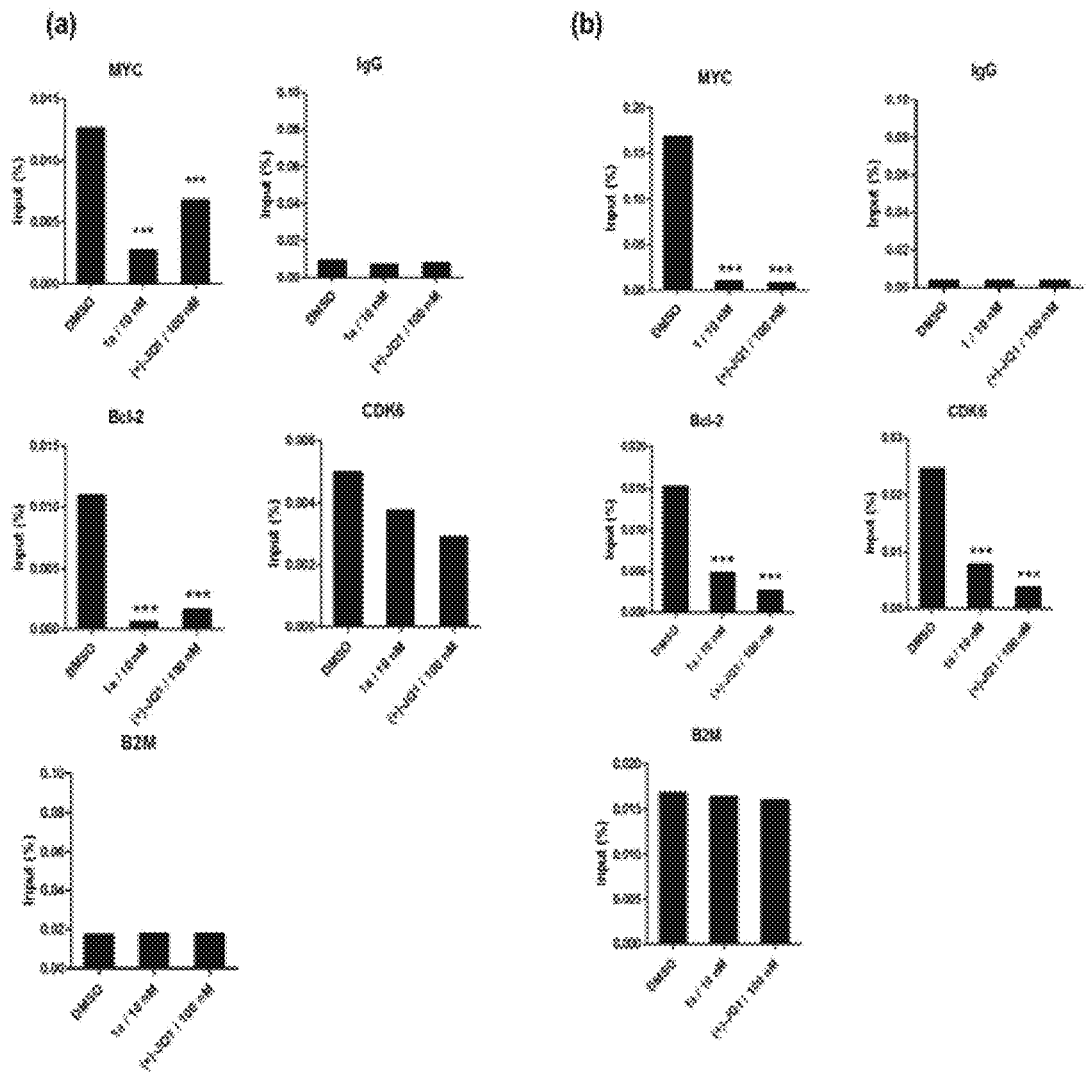
FIG. 4 Chromatin immunoprecipitation (ChIP) analysis showed that 1a selectively decreased the binding of BRD4 to MYC, Bcl-2 and CDK6, but not housekeeping genes (B2M) in (a) A375 and (b) A2058cells. Bar graphs represented the mean enrichment relative to input and error bars reflect standard deviation of results derived from biological triplicate experiments. Significantly different at ***p<0.01. Error bars represent the standard deviations of the results from three independent experiments.

To further verify the BRD4 inhibitory activity of iridium (III) complex 1a, the complex was subjected to a dose-response experiment in the TR-FRET assay. The results showed that 1a inhibited the peptide-binding activity of BRD4 with an $IC_{50}$ value (dose required to inhibit 50% TR-FRET ratio) of 0.07 µM (FIG. 4a). The inhibitory activity of complex 1a against the interaction between BRD4 and H4AcK4 was further confirmed using an AlphaScreen assay.

Figure 3:
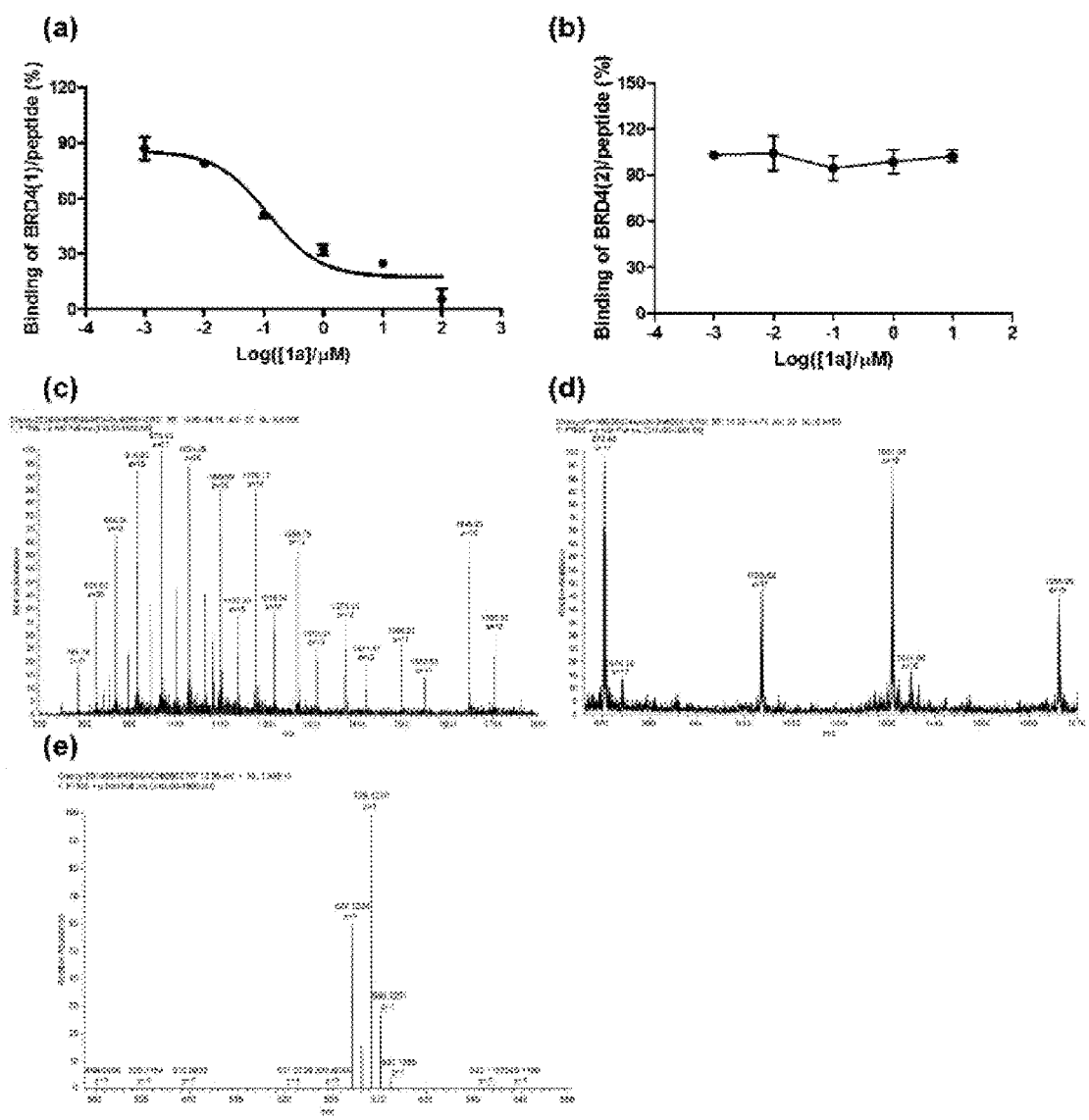
FIG. 3 shows the ability of Compound 1a to displace H4AcK4 peptide from (a) BRD4(1) and (b) BRD4(2) in a time-resolved-fluorescent resonance electron transfer (TR-FRET) assay. Binding of H4AcK4 to BRD4(1) was strongly inhibited by 1a, with half-maximum inhibitory concentration ($IC_{50}$) value of 0.07 μM. Error bars represent the standard deviations of the results from three independent experiments. LC-MS/MS analysis of (c) BRD4(1), (d) BRD4(1) with 1a and (e) 1a only. BRD4(1) and 1a complex were buffered in 10 mM Tris-HCl, pH=7.5, 500 mM NaCl and incubated at 25° C. for 2 h. The sample was analyzed by positive ion mass spectra.

BRD4 contains two conserved N-terminal broinodomains BRD4(1) and BRD4(2). The activity of complex 1a against the binding of BRD4(2) to H4AcK4 was also investigated using the TR-FRET assay (FIG. 3b). The results revealed that 1a exhibited no significant inhibition of the interaction between BRD4(2) and H4AcK4. Therefore, complex 1a selectively inhibits the BRD4(1) domain. This result was further corroborated by a fluorescence polarization assay.

The interaction between complex 1a with the BRD4 proteins was also monitored by luminescence spectroscopy, since complex 1a exhibits a high luminescence response in the presence of BRD4(1) and BRD4(2). A time-course experiment revealed that the luminescence signal of 1a reached steady-state within 5 and 8 min upon the addition of BRD4(1) or BRD4(2) at 25° C., respectively. These data suggest that complex 1a may react slightly faster with the BRD4(1) protein.

LC-MS/MS further demonstrated the binding of 1a to BRD4(1). Mass spectrometer data was pooled and analyzed for the BRD4(1)-1a complex of 17036.5 Da or the intact BRD4(1) corresponding to 16472.3 Da (FIGS. 3c and 3d). As shown in FIG. 3e, MS/MS fragmentation of the singly-charged ion (m/z 529.1) matched the molecular weight of 1a with cleavage of two ACN (acetonitrile) ligands. After 2 h of incubation with 1a, a complex was observed corresponding to BRD4(1) binding to $C_{24}H_{20}N_2Ir$ (529.1) with an additional buffer adduct $NH_4^+OH^-$ (35.0). The MS data therefore suggests that 1a loses two ACN ligands upon binding to BRD4(1).

To further investigate the mechanism of action of 1a, we incubated the complex in DMSO solution. The results showed that 1a exchanges its acetonitrile ligands for DMSO ligands from the solution. This is similar to previous complexes,[42] as well as NAMI-A and KP1019. Moreover, since DMSO ligands are also labile, this should not affect the ability of 1a to bind covalently to the protein target, as is the case for the previously described complexes. This makes the mechanism of 1a likely to be similar to that of NAMI-A/KP1019 which also interact covalently with their biomolecular targets via ligand exchange. Furthermore, after ligand exchange with DMSO, the complex was stable for at least 24 h in DMSO solution and in plasma under our test conditions, as revealed by the absence of significant changes in the absorbance.

Figure 5:
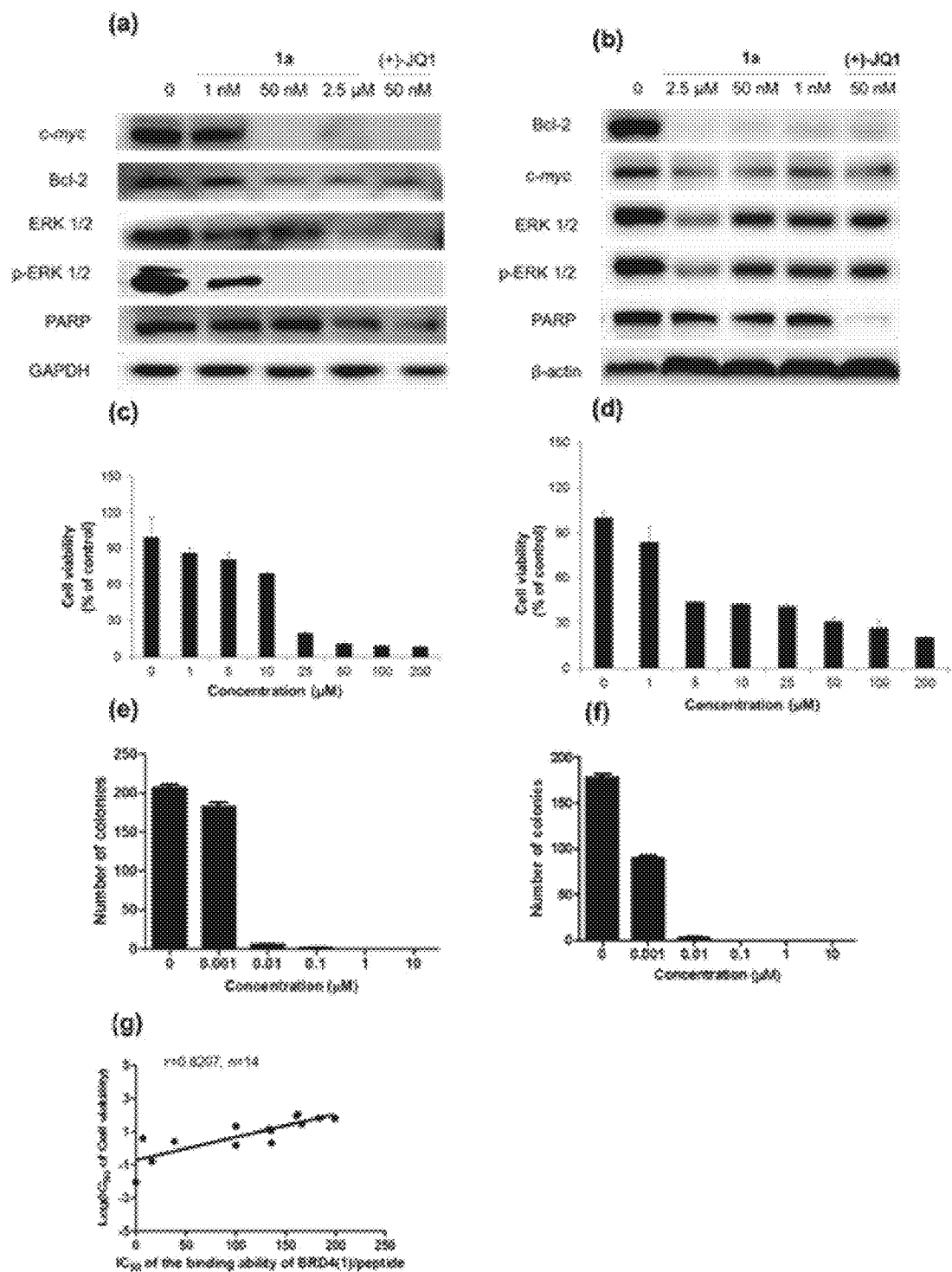
FIG. 5. shows an immunoblotting analysis of the effect of 1a and (+)-JQ1 treatment in (a) A375 and (b) A2058 cells, Densitometry analysis revealed that 1a inhibited c-myc, Bcl-2, ERK ½, p-ERK ½and PARD expression. Dose response analysis of cell viability of complex 1a against (c) A375 cells and (d) A2058 cells. Error bars represent the standard deviations of the results from three independent experiments. Normalized proliferation curves in the colony formation assay for (e) A375 and (f) A2058 cells treated with vehicle or 1a (0.001-10 μM) measured by crystal violet staining. Error bars represent the standard deviations of the results from three independent experiments. (g) The relationship between the $IC_{50}$ of the binding ability of BRD4 (1)/peptide and the log of $IC_{50}$ of A375 cell viability, and a trend of positive correlation was observed (r=0.8207, n=14).

Given by the promising activity of complex 1a at antagonizing the BRD4-H4AcK4 interaction in vitro, the complex was further examined for its biological activity in cells. We first performed a chromatin immunoprecipitation (ChIP) assay to investigate whether 1a can modulate the binding of BRD4 to chromatin in human malignant melanoma A375 and human caucasian metastatic melanoma A2058 cell lines (FIG. 5). ChIP analysis at the MYC promoter showed that 10 nM of complex 1a decreased the recruitment of BRD4 after 6 h. A similar pattern was observed at Bcl-2 and CDK6 loci, but not at the housekeeping B2M gene. These results suggest that 1a is able to modulate the interaction between chromatin and BRD4 in A375 and A2058 cells, particularly at the MYC promoter.

Figure 6:
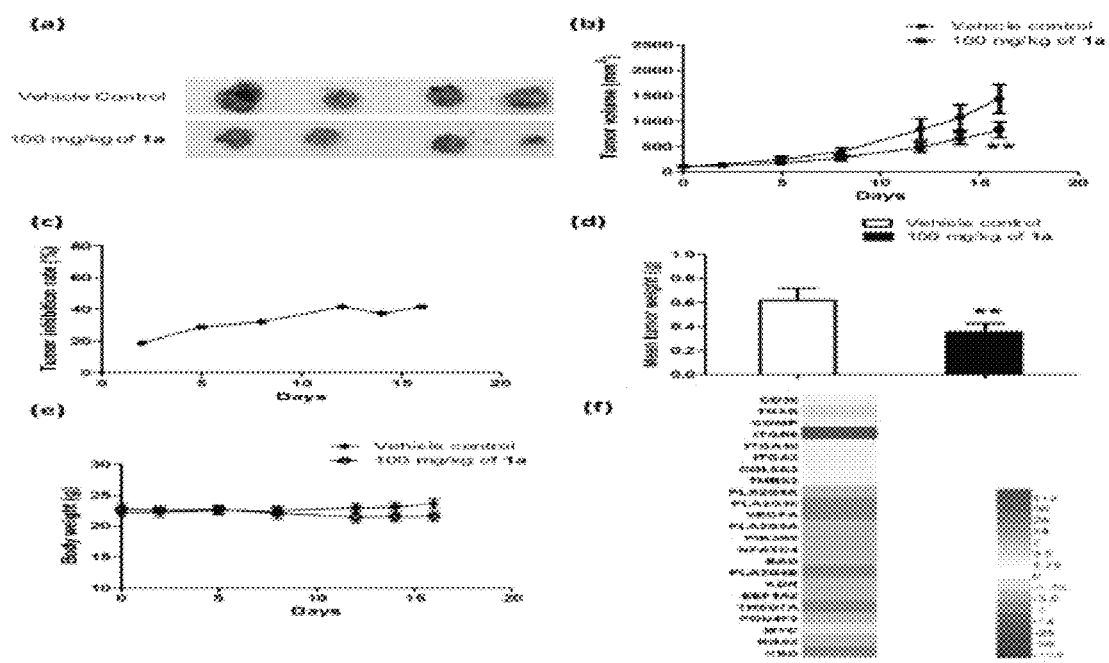
FIG. 6 shows the anti-proliferative activity of 1a in an in vivo xenograft model of melanoma. (a) Photographs of dissected tumors from the control (vehicle) and treatment (1a, 100 mg/kg). (b) Average A375 tumour volume in the control group and treatment group (1a, 100 mg/kg). Each group contained six mice and results are reported as the values of the mean±SEM. (c) Tumour inhibition of A375 xenografts in the treatment group (1a, 100 mg/kg) expressed as percentage reduction in tumor volume compared to the control group. The results were analyzed using the Student's t-test. Significantly different at 0.01<p<0.05. d) Average tumor weight of the vehicle control group versus the treatment group (1a, 100 mg/kg). e) Average body weight of the two groups. Each group contained six mice, and results were reported as the values of the mean±SEM. The results were analyzed using the Student's t-test. Significantly different at 0.01<p<0.05. f) Heat map of regulated genes of the ECM pathway and VEGF signaling pathway following treatment with 1a. The color scale in the inset represents the log-fold change of expression compared with untreated control.

Furthermore, the impact of complex 1a on c-myc and Bcl-2 expression in A375 and A2058 cells was investigated. Immunoblotting analysis of lysates from treated cells revealed that the expression of c-myc and Bcl-2 proteins was reduced by 1a in a dose-dependent mariner (FIG. 6). These observations are also consistent with the result of the chip assay described above, which showed that complex 1 could disrupt the binding of BRD4 to the MYC and Bcl-2 promoters. These results therefore suggest that 1a may act as a transcriptional modulator of c-myc and Bcl-2 expression.

c-myc and Bcl-2have been intensely studied as anti-cancer targets due to their roles in cell cycle progression, cellular transformation and apoptosis. Therefore, we were interested to investigate whether or not complex 1a could exhibit anti-proliferative effects against cancer cells. In in vitro evaluation, complex 1a exhibited potent cytotoxicity against the A375 ($IC_{50}$=12.5 µM) and A2058 ($IC_{50}$=3 µM) cell lines (FIGS. 6c and 6d). The anti-proliferative activity of complex 1a towards A375 and A2058 cells was further determined using the colony formation assay. The results showed that 1a was cytotoxic against A375 and A2058 melanoma cells with estimated $IC_{50}$ values (dose required to inhibit 50% cellular growth after 24 h exposure to 1a) of 5 nM and 1 nM, respectively. We reason that the cytotoxicity imparted by 1a could be atuibuted, at least in part, to the suppression of c-mvc and Bcl-2 transcription via BRD4 inhibition Additionally, ERK ½, p-ERK ½ and PARP expression were also down-regulated in A375 and A2058 cells after treatment with 1a (FIGS. 6a and 6b). Aberrant ERK ½ activation is implicated in numerous tumors, while PARP promotes cell survival due to its role in DNA repair. Therefore, the inhibition of ERK ½ and/or PARP activity by complex 1a may represent an alternative mechanism by which the complex exerts anti-proliferative activity.

To further explore the relationship between BRD4 inhibition and cytotoxic activity, we also tested the metal complexes 1, 1a-1j for their in vitro anticancer activity against A375 cells. Plotting the antiproliferative $IC_{50}$ values of the complexes against the $IC_{50}$ values for the inhibition of BRD4(1)-H4AcK4binding revealed a positive relationship (r=0.8207, n=14) (FIG. 5g), suggesting that the anticancer activity of the metal complexes may be mediated by their inhibition of BRD4 binding activity To further investigate the antitumor activity exerted by BRD4 inhibition, we explored the biological activity of 1a in a mouse xenograft tumor model. Six to seven week-old male CB.17 SCID mice were injected subcutaneously with human malignant melanoma A375 cells, and after the establishment of palpable tumors, were administrated with 1a (100 mg/kg) or vehicle (13% DMSO in normal saline) intraperitoneally (i.p.) once daily for 16 days. Encouragingly, the treated tumors were ca. 40% smaller than the control tumors over the course of the treatment, with a significant difference in estimated tumor volume being observed after 16 days (FIGS. 6a, 6b and 6c). Tumor weight measurements after sacrifice confirmed a reduction in tumor growth in mice administrated with 1a (FIG. 6d). We also observed that the treated mice exhibited no signs of weight loss over the course of the experiment (FIG. 6e), Taken together, these results indicate that complex 1a significantly inhibited the growth of melanoma tissue in an in vivo xenograft model, without causing overt toxicity to the mice.

Microarray analysis was performed on the excised tumor tissues to identify signaling pathways that were up-regulated or down-regulated by complex 1a. The results showed that treatment with 1a resulted in MYC down-regulation as well as a significant decrease in expression of the c-Myc target gene set in the tumor tissues. Moreover, complex 1a up-regulated genes in the extracellular matrix (ECM) pathway while down-regulating genes in the VEGF signaling pathway (FIG. 6f). Differential ECM gene expression is an important marker of metastatic activity, and BRD4 modulates the expression of many ECM genes that are dysregulated in tumors. Moreover, increased MYC activity can also suppress ECM gene expression[53-55]. Hence, the up-regulation of the ECM pathway in tumor tissues could potentially be attributed to the inhibition of BRD4-directed transcription by 1a in vivo. Furthermore, MYC promotes angiogenesis through the up-regulation of VEGF.[56, 57] Therefore, the down-regulation of genes in the VEGF signaling pathway could also be attributed to the effects of 1a on BRUT-mediated transcription in vivo.

Alphascreen assay, Assays were performed as described previously with minor modifications from the manufacturer's protocol (PerkinElmer, USA). All reagents were diluted in 50 mM HEPES, 100 mM NaCl, 0.1% BSA, pH 7.4 supplemented with 0.05% CHAPS and allowed to equilibrate to room temperature prior to addition to plates. A 24-point 1:2 serial dilution of the ligands was prepared over the range of 0-150 μM and 4 μL transferred to low-volume 384-well plates (ProxiPlate™-384 Plus, PerkinElmer, USA), followed by 4 μL of His-tagged protein (BRD4(1), 250 nM, BRD4(2) and CREBBP, 2000 nM, Cayman Chemical, Ann Arbor, Mich., USA). Plates were sealed and incubated at room temperature for 30 min, before the addition of 4 μL of biotinylated peptide at equimolar concentration to the protein [peptide for BRD4(1) & BRD4(2): HSGRGK(Ac)GGK(Ac)GLGK(Ac)GGAK(Ac)RHRK(Biotin)-OH peptide for CREBBP: Biotin-KSAPATGGVK(Ac)KPHRYRPGT-OH (China peptide, Shanghai, China)]. 384-well plates were sealed and incubated for a further 30 min, before the addition of 4 μL of streptavidin-coated donor beads (25 μg/mL) and 4 μL nickel chelate acceptor beads (25 μg/mL) under low light conditions. Plates were foil-sealed to protect from light, incubated at room temperature for 60 min and read on an EnVision Multilabel Reader (PerkinElmer) using an AlphaScreen 680 excitation/570 emission filter set. IC50 values were calculated in Prism 5 (GraphPad Software, USA) after normalization against corresponding dimethyl sulfoxide (DMSO) controls and are given as the final concentration of compound in the 20 μL reaction volume.

Fluorescence polarization assay. All components were dissolved in buffer composition of 50 mM HEPES pH 7.4, 150 mM NaCl and 0.5 mM CHAPS with final concentrations of BRD4(1) or BRD4(2), fluorescent ligand H4K5acK8acK12acK16ac, HSGRGK(Ac)GGK(Ac)GLGK(Ac)GGAK(Ac)RHRK(FAM) 100 nM. 10 μL of this reaction mixture was added to wells containing 10 μL of various concentrations of test compound or DMSO vehicle (1% final) in 384-well black plate (PerkinElmer) and equilibrated in the dark for 60 min at room temperature. Fluorescence anisotropy was measured by SpectraMax M5 microplate reader (Molecular Devices) using FP module with excitation and emission wavelengths are 485 nm and 520 nm respectively.

Measurement of caspase-6 activity in vitro. Caspase-6 activity assay was performed using a fluorometric method (Abnova, Taiwan) according to the manufacturer's instructions. Serial dilution of 1a were mixed with reaction buffer and 50 μM VEID-AFC (AFC, 7-amino-4-trifluoromethyl coumarin) substrate. The mixture was incubated at 37° C. for 1 h. Measured the fluorescence at an excitation and emission wavelength of 400 nm and 505 nm using SpectraMax M5 microplate reader (Molecular Devices).

STAT3 DNA-binding ELISA, The STAT3 DNA-binding assay was performed using the TransAM® Transcription Factor ELISA (Active Motif, Carlsbad, Calif.) according to the manufacturer's instructions. Briefly, HepG2 cells nuclear extract (2 μg) containing activated STAT3 was added with compound (20 μL) and complete binding buffer (30 μL) to microlitre wells coated with the STAT3 DNA consensus sequence. The mixture was incubated at room temperature for 1 h. The wells were washed three times with 1 x wash buffer, and incubated with STAT3 antibody for 1 h. The wells were washed as before and incubated with horseradish peroxidase-conjugated secondary antibody at room temperature for 1 h. The wells were washed as before, incubated with 100 μL of developing solution, quenched with 100 μL stop solution, and the absorbance was measured at λ=450 nm.

3-(4,5-Dimethylthiazol-2-yl)-2,5-Diphenyltetrazolium Bromide (MTT) assay. Cells were seeded in 96-well plates in triplicate at a density of 5,000 cells per well and given 24 h to adhere. Cells were then treated with varying concentrations of the tested compounds in the presence of 10% FBS. The cells were incubated for 72 h at 37° C. 25 μL of MTT dye was added to each sample and. incubated for 3.5 h. After this, 100 μL of DMSO was added to each well. The absorbance at 450 nm was recorded and the Half-Maximal inhibitory concentrations (IC50) were determined using Prism 5.0 (Graph-Pad Software Inc., San Diego, Calif., USA)

Colony formation assay. Cells were seeded at 250 cells per well in 6 cm well plates (n=3). After 7 to 10 days of treatment, cells were stained with crystal violet, photographed, and scored.

REFERENCES

The following articles are referenced in the text and incorporated herein by reference in their entirety.
1. B. Li, M. Carey and J. L. Workman, Cell, 2007, 128, 707-719.
2. G. E. Zentner and S. Henikoff, Nat. Struct. Mol. Biol., 2013, 20, 259-266 .
3. A. J. Ruthenburg, H. Li, D. J. Patel and C. David Allis, Nat. Rev. Mol. Cell Biol., 2007, 8, 983-994.
4. C. H. Arrowsmith, C. Bountra, P. V. Fish, K. Lee and M. Schapira, Nat. Rev. Drug Discov., 2012, 11, 384-400.
5. S. D. Taverna, H. Li, A. J. Ruthenburg, C. D. Allis and D. J. Patel, Nat. Struct. Mol. Biol., 2011, 55, 576-586.
6. C.-w. Chung, A. W. Dean, J. Woolven and P. Bamborough, J. Med. Chem., 2001, 55, 576-586.
7. L. Zeng and M.-M. Zhou, FEBS Lett., 2002, 513, 124-128.
8. B. Florence and D. V. Faller, Front. Biosci., 2001, 6, D1008-D1018.
9. C.-w. Chung and D. F. Tough, Drug Discovery Today: Therapeutic Strategies, 2012, 9, e111-e120.
10. Z. Yang, N. He and Q. Zhou, Mol. Cell. Biol., 2008, 28, 967-976.
11. A. Dey, A. Nishiyama, T. Karpova, J. McNally and K. Ozato, Mol. Biol. Cell, 2009, 20, 4899-4909 .
12. M. F. Segura, B. Fontanals-Cirera, A. Gaziel-Sovran, M. V. Guijarro, D. Hanniford, G. Zhang, P. Gonzalez-Gomez, M. Morante, L. Jubierre, W. Zhang, F. Darvishian, M. Ohlmeyer, I. Osman, M. M. Zhou and E. Hernando, Cancer Res., 2013, 73, 6264-6276.

13. P. Filippakopoulos, J. Qi, S. Picaud, Y. Shen, W. B. Smith, O, Fedorov, E. M. Morse, T. Keates, T. T. Hickman, I. Felletar, M. Philpott, S. Munro, M. R. McKeown, Y. Wang, A. L. Christie, N. West, M. J. Cameron, B. Schwartz, T. D. Heightman, N. La Thangue, C. A. French, O. Wiest A. L. Kung, S. Knapp and J. E. Bradner, *Nature*, 2010, 468, 1067-1073.
14. Jake E. Delmore, Ghayas C. Issa, Madeleine E. Lemieux, Peter B. Rahl, J. Shi, Hannah M. Jacobs, E. Kastritis, Gilpatrick, Ronald M. Paranal, J. Qi, M. Chesi, Anna C. Schinzel, Michael R. McKeown, Timothy P. Heffernan, Christopher R. Vakoc, P. L. Bergsagel, Irene M. Ghobrial, Paul G. Richardson, Richard A. Young, William C. Hahn, Kenneth C. Anderson, Andrew L. Kung, James E. Bradner and Constantine S. Mitsiades, *Cell*, 2011, 146, 904-917.
15. J. A. Mertz, A. R. Conery, B. M. Bryant, P. Sandy, S. Balasubramanian, D. A. Mele, L. Bergeron and R. J. Sims, *Proc. Natl. Acad. Sci. USA*, 2011, 108, 16669-16674.
16. C. G. Hartinger and P. J. Dyson, *Chem. Soc. Rev.*, 2009, 38, 391-401.
17. A. V. Klein and T. W. Hambley, *Chem. Rev.*, 2009, 109, 4911-4920.
18. G. Gasser, I. Ott and N. Metzler-Nolte, *J. Med. Chem.*, 2010, 54, 3-25.
19. A. L. Noffke, A. Habtemariarm, A. M. Pizarro and P. J. Sadler, *Chem. Commun.*, 2012, 48, 5219-5246.
20. A. Meyer, C. P. Bagowski, M. Kokoschka, M. Stefanopoulou, H. Alborzinia, S. Can, D. H. Vlecken, W. S. Sheldrick, S. Wolfl and I. Ott, *Angew. Chem. Int. Ed. Engl.*, 2012, 51, 8895-8899.
21. A. de Almeida, B. L. Oliveira, J. D. G. Correia, G. Soveral and A. Casini, *Coord. Chem. Rev.*, 2013, 257, 2689-2704.
22. C. G. Hartinger, M. Groessl, S. M. Meier, A. Casini and P. J. Dyson, *Chem. Soc. Rev.*, 2013, 42, 6186-6199.
23. H. Huang, P. Zhang, B. Yu, Y. Chen, I Wang, L. Ji and H. Chao, *J. Med. Chem.*, 2014, 57 8971-8983.
24. A. Leonidova, V. Pierroz, L. A. Adams, N. Barlow, S. Ferrari, B. Graham and G. Gasser, *ACS Med. Chem. Lett.*, 2014, 5, 809-814.
25. D.-L. Ma, W.-L, Wong, W.-H. Chung, F.-Y. Chan, P,-K. So, T.-S. Lai, Z.-Y. Zhou, Y.-C. Leung and K.-Y. Wong, *Angew. Chem. Int. Ed. Engl.*, 2008, 47, 3735-3739.
26. E. Meggers, *Chem. Commun.*, 2009, 1001-1010.
27. X. Meng, M. L. Leyva, M. Jenny, I. Gross, S. Benosman, B. Pricker, S. Harlepp, P, Hèbraud, A. Boos, P. Wlosik, P. Bischoff, C. Sirlin, M. Pfeffer, J-P. Loeffler and C. Gaiddon, *Cancer Res.*, 2009, 69, 5458-5466.
28. C. M. Che and F. M. Siu, *Curr. Opin. Chem. Biol.*, 2010, 14, 255-261.
29. K. J. Kilpin and P. J. Dyson, *Chem. Sci.*, 2013, 4, 1410-1419.
30. J. Singh, R. C. Petter, T. A. Baillie and A. Whitty, *Nat. Rev. Drug Discov.*, 2011, 10, 307-317.
31. L. Feng, Y. Geisselbrecht, S. Blanck, A. Wilbuer, G. E. Atilla-Gokcumen, P. Filippakopoulos, K. Kräling, M. A. Celik, K. Harms, J. Maksimoska, R. Marmorstein, G. Frenking, S. Knapp, L.-0. Essen and E. Meggers, *J. Am. Chem. Soc.*, 2011, 133, 5976-5986.
32. S. Blanck, Y. Geisselbrecht, K. Kraling, S. Middel, T. Mietke, K. Harms, L.-O. Essen and E. Meggers, *Dalton Trans.*, 2012, 41, 9337-9348.
33. C. H. Leung, H. J. Zhong, H. Yang, Z. Cheng, D. S. H. Chan, V.P.Y. Ma, R. Abagyan, C. Y. Wong and D. L. Ma, *Angew. Chem. Int. Ed. Engl.*, 2012, 51, 9010-9014.
34. S. Dieckmann, R. Riedel, K. Harms and E. Meggers, *Eur. J. Inorg. Chem.*, 2012, 2012, 813-821.
35. S. Mollin, S. Blanck, K. Harms and E. Meggers, *Inorganica Chim. Acta*, 2012, 393, 261-268.
36. R. Anand, J. Maksimoska, N. Pagano, E. Y. Wong, P. A. Gimotty, S. L. Diamond, E. Meggers and R. Marmorstein, *J. Med. Chem.*, 2009, 52, 1602-1611.
37. G. E. Atilla-Gokcumen, L. Costanzo and E. Meggers, *J. Biol. Inorg. Chem.*, 2011, 16 45-50.
38. S. Blanck, T. Cruchter, A. Vultur, R. Riedel, K. Harms, M. Herlyn and E. *Meggers, Organometallics*, 2011, 30 4598-4606.
39. C. Streu, L. Feng, P. J. Carroll, J. Maksirnoska, R. Marmorstein and E. Meggers, *Inorganica Chim. Acta*, 2011, 377, 34-41.
40. M. S. Lowry, W. R. Hudson, R. A. Pascal and S. Bernhard, *J. Am. Chem. Soc.*, 2004, 126, 14129-14135.
41. D. L. Ma, W. L. Wong, W. H. Chung, F. Y. Chan, P. K. So, T. S. Lai, Z. Y. Zhou, Y. C. Leung and K. Y. Wong, *Angew. Chem. Int. Ed. Engl.*, 2008, 47, 3735-3739.
42. C. Li, M. Yu, Y. Sun, Y. Wu, C. Huang and F. Li, *J. Am. Chem. Soc.*, 2011, 133, 11231-11239.
43. F. Piccioli, S. Sabatini, L. Messori, P. Orioli, G. Hartinger Ch and B. K. Keppler, *J. Inorg. Biochem.*, 2004, 98, 1135-1142.
44. A. R. Timerbaev, L. S. Foteeva, A. V. Rudnev, J. K. Abramski, K. Polec-Pawlak, C. G. Hartinger, M. Jarosz and B. K. Keppler, *Electrophoresis*, 2007, 28, 2235-2240.
45. O. Domotor, C. G. Hartinger, A. K. Bytzek, T. Kiss, B. K. Keppler and E. A. Enyedy, *J. Biol. Inorg. Chem.*, 2013, 18, 9-17.
46. R. Trondl, P. Heffeter, C. R. Kowol, M. A. Jakupec, W. Berger and B. K. Keppler, *Chem. Sci.*, 2011, 5, 2925-2932.
47. M. I. Webb and C. J. Walsby, *Dalton Trans.*, 2015, DOI: 10.1039/c5dt02021b.
48. F. Kratz, M. Hartmann, B. Keppler and L. Messori, *J. Biol. Chem.*, 1994, 269 2581-2588.
49. L. Messori, P. Orioli, D. Vullo, E. Alessio and E. Iengo, *Eur. J. Biochem.*, 2000, 267, 1206-1213.
50. M. A. Stoff-Khalili, P. Dall and D. T. Curiel, *Cancer Gene Ther.*, 2006, 13, 633-647.
51. K. J. Falkenberg and R. W. Johnstone, *Nat. Rev. Drug Discov.*, 2014, 13, 673-691.
52. N. P. S. Crawford, J. Alsarraj, L. Lukes, R. C. Walker, J. S. Officewala, H. H. Yang, M. P. Lee, K. Ozato and K. W. Hunter, *Proc. Natl. Acad. Sci, USA*, 2008, 105, 6380-6385.
53. H. A. Coller, C. Grandori, P. Tamayo, T. Colbert, E. S. Lander, R. N. Eisenman and T. R. Golub, *Proc. Natl. Acad. Sci. USA*, 2000, 97, 3260-3265.
54. J. D. Watson, S. K. Oster, M. Shago, F. Khosravi and L. Z. Penn, *J Biol. Chem.*, 2002, 277, 36921-36930.
55. E. R. Lawlor, L. Soucek, L. Brown-Swigart, K. Shchors, C. U. Bialucha and G. I. Evan, *Cancer Res.*, 2006, 66, 4591-4601.
56. R. Chen, J. H. Yik, Q. J. Lew and S. H. Chao, *BioMed research international*, 2014, 2014, 232870.
57. S. W. J. Ember, J. Y. Zhu, S. H. Olesen, M. P. Martin, A. Becker, N. Berndt, G. I. Georg and E. Schönbrunn, *ACS Chem. Biol.*, 2014, 9, 1160-1171.
58. P.B. Rahl, C. Y. Lin, A. C. Seila, R. A. Flynn, S. McCuine, C. B. Burge, P. A. Sharp and R. A. Young, *Cell*, 2010, 141, 432-445.

What we claim is:

1. A compound of the formula:

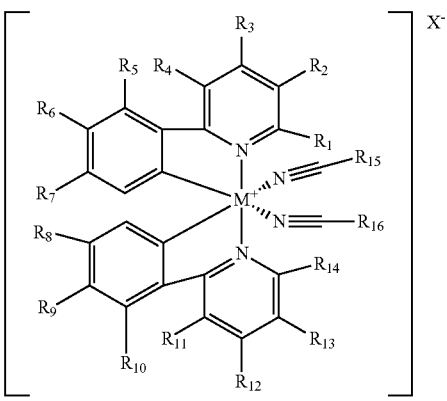

wherein X' is an anion selected from trifluoromethanesulfonate, hexafluorophosphate, chloride perchlorate, tetrafluorohorate tetraphenyl borate, or substituted tetraphenyl borate;
M is iridium;
$R_1$ and $R_{14}$ are each individually selected from the group consisting of methyl and ethyl;
$R_2$, $R_3$ $R_6$, $R_9$, $R_{12}$ and $R_{13}$ are each individually selected from the group consisting of hydrogen, alkyl and alkoxy groups containing from 1-6 carbon atoms wherein the alkyl group is linear or branched;
$R_7$ and $R_8$ are each individually selected from the group consisting of hydrogen, CHO, alkyl of from 2-6 carbon atoms and alkoxy groups containing from 1-6 carbon atoms wherein the alkyl group is linear or branched
$R_4$ and $R_5$ are each individually selected from the group consisting of hydrogen, alkyl and alkoxy groups containing from 1-6 carbon atoms wherein the alkyl group is linear or branched or R4 and $R_5$ can jointly form a CH=CH or $CH_2$—$Ch_2$ group; and
$R_{10}$ and $R_{11}$ are each individually selected from the group consisting of hydrogen, alkyl and alkoxy groups containing from 1-6 carbon atoms wherein the alkyl group is linear or branched or $R_{10}$ and $R_{11}$ can jointly form a CH=CH or $CH_2$—$CH_2$ group;
$R_{15}$ and $R_{16}$ are each individually selected from alkyl groups of from 1-4 carbon atoms or aryl groups of 6-10 carbon atoms.

2. A compound as claimed in claim 1 of the formula:

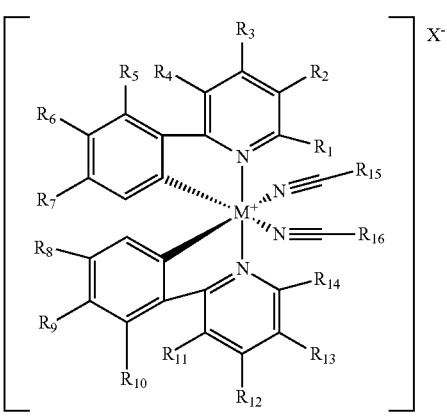

wherein X and $R_1$-$R_{16}$ have the same meaning as in claim 1.

3. The compound as claimed in claim 1, wherein $R_1$ and $R_{14}$ are both methyl.

4. A compound as claimed in claim I, wherein each of $R_2$, $R_3$, $R_4$, $R_5$, $R_6$, $R_7$, $R_8$, $R_9$, $R_{10}$, $R_{11}$ $R_{12}$ and $R_{13}$ is hydrogen or methyl.

5. A compound as claimed in claim 4, wherein each of $R_2$, $R_3$, $R_4$, $R_5$, $R_6$, $R_7$, $R_8$, $R_9$, $R_{10}$, $R_{11}$ $R_{12}$ and $R_{13}$ is hydrogen.

6. A compound as claimed in claim 5, which is:

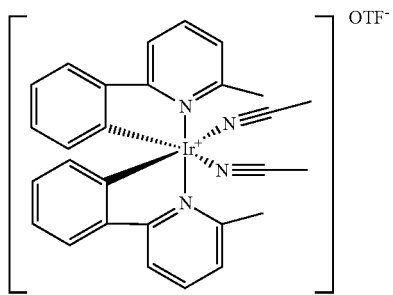

wherein OTF indicates that the compound is a trifluoromethanesulfonate salt.

7. A method of inhibiting transcriptional regulators selected from bromodomain and extraterminal bromodomain to inhibit proliferation of metastatic cancer cells which comprises administering a therapeutic dose of a compound of the formula

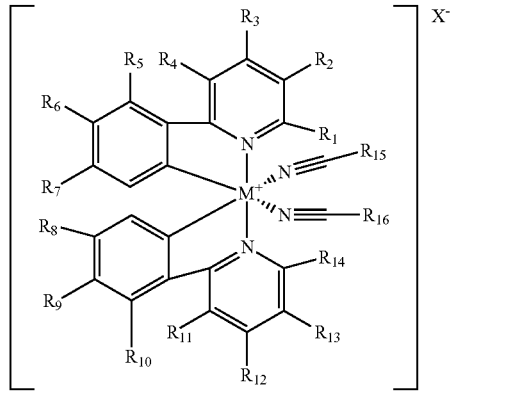

wherein $X^-$ is an anion selected from trifluoromethanesulfonate, hexafluorophosphate, chloride, perchlorate, tetrafluoroborate tetraphenyl borate, or substituted tetraphenyl borate such as tetra[3,5-bis(trifluoromethyl) phenyl] borate
M is iridium or rhodium;
$R_1$ and $R_{14}$ are each individually selected from the group consisting of methyl and ethyl;
$R_2$, $R_3$ $R_6$, $R_9$, $R_{12}$ and $R_{13}$ are each individually selected from the group consisting of hydrogen, alkyl and alkoxy groups containing from 1-6 carbon atoms wherein the alkyl group is linear or branched;
$R_7$ and $R_8$ are each individually selected from the group consisting of hydrogen, CHO, alkyl of from 1-6 carbon atoms and alkoxy groups containing from 1-6 carbon atoms wherein the alkyl group is linear or branched
$R_4$ and $R_5$ are each individually selected from the group consisting of hydrogen, alkyl and alkoxy groups containing from 1-6 carbon atoms wherein the alkyl group is linear or branched or R4 and R5 can jointly form a CH=CH or $CH_2$—$CH_2$ group; and $R_{10}$ and $R_{11}$ are each individually selected from the group consisting of hydrogen, alkyl and alkoxy groups containing from 1-6 carbon atoms wherein the alkyl group is linear or branched or $R_{10}$ and $R_H$ can jointly form a CH=CH or $CH_2$—$CH_2$ group; and $R_{15}$ and $R_{16}$ are each individually selected from alkyl groups of from 1-4 carbon atoms or aryl groups of 6-10 carbon atoms, to a patient in need thereof.

8. A method as claimed in claim 7, wherein said transcriptional regulator is BRD4.

9. A method as claimed in claims 8, herein said metastatic cancer cells are metastatic melanoma cells.

10. A method as claimed in claim 8, wherein said compound of the formula:

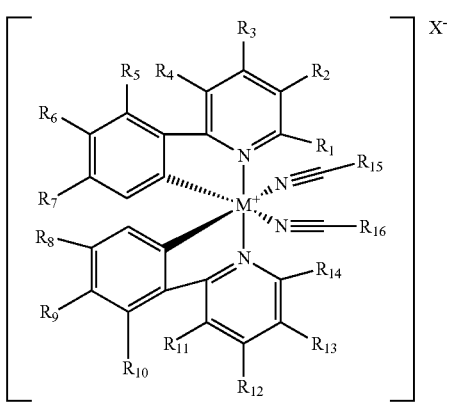

wherein $X^-$ is an anion selected from trifluoromethanesulfonate, hexafluorophosphate, chloride perchlorate, tetrafluoroborate tetraphenyl borate, or substituted tetraphenyl borate;

M is iridium;

$R_1$ and $R_{14}$ are each individually selected from the group consisting of methyl and ethyl;

$R_2$, $R_3$ $R_6$, $R_9$, $R_{12}$ and $R_{13}$ are each individually selected from the group consisting of hydrogen, alkyl and alkoxy groups containing from 1-6 carbon atoms wherein the alkyl group is linear or branched;

$R_7$ and $R_8$ are each individually selected from the group consisting of hydrogen, CHO, alkyl of from 2-6 carbon atoms and alkoxy groups containing from 1-6 carbon atoms wherein the alkyl group is linear or branched $R_4$ and $R_5$ are each individually selected from the group consisting of hydrogen, alkyl and alkoxy groups containing from 1-6 carbon atoms wherein the alkyl group is linear or branched or $R_4$ and $R_5$ can jointly form a CH=CH or $CH_2$—$CH_2$ group; and $R_{10}$ and $R_{11}$ are each individually selected from the group consisting of hydrogen, alkyl and alkoxy groups containing from 1-6 carbon atoms wherein the alkyl group is linear or branched or $R_{10}$ and $R_{11}$ can jointly form a CH=CH or $CH_2$—$CH_2$ group;

$R_{15}$ and $R_{16}$ are each individually selected from alkyl groups of from 1-4 carbon atoms or aryl groups of 6-10 carbon atoms.

11. The Method as claimed in claim 8, wherein $R_1$ and $R_{14}$ are both methyl.

12. The method as claimed in in claim 10, wherein each of $R_2$, $R_3$, $R_4$, $R_5$, $R_6$, $R_7$, $R_8$, $R_9$, $R_{10}$, $R_{11}$ $R_{12}$ and $R_{13}$ is hydrogen or methyl.

13. The method as claimed in claim 12, wherein each of $R_2$, $R_3$, $R_4$, $R_5$, $R_6$, $R_7$, $R_8$, $R_9$, $R_{10}$, $R_{11}$, $R_{12}$ and $R_{13}$ is hydrogen.

14. The method as claimed in claim 13, wherein said compound is:

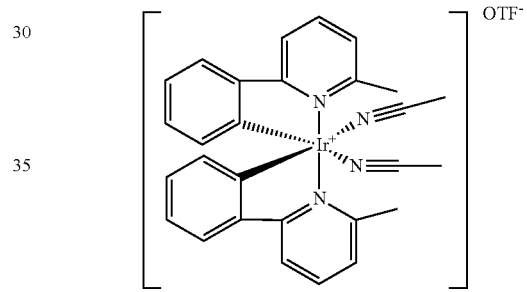

wherein OTF indicates that the compound is a trifluoromethanesulfonate salt.

* * * * *